United States Patent [19]

Uhrhan et al.

[11] 4,101,506

[45] Jul. 18, 1978

[54] CYANAMIDE STABILIZERS

[75] Inventors: Paul Uhrhan; Reinhard Lantzsch, both of Cologne; Harald Oertel; Ernst Roos, both of Odenthal; Dieter Arlt, Cologne, all of Germany

[73] Assignee: Bayer Aktiengesellschaft, Leverkusen, Germany

[21] Appl. No.: 730,202

[22] Filed: Oct. 6, 1976

[30] Foreign Application Priority Data

Oct. 11, 1975 [DE] Fed. Rep. of Germany ....... 2545646

[51] Int. Cl.$^2$ ..................... C08K 5/34; C07D 211/06
[52] U.S. Cl. .......................... 260/45.8 N; 260/293.86; 260/293.87; 260/293.88; 260/293.89; 260/293.9
[58] Field of Search ................... 260/293.86, 293.87, 260/293.88, 293.89, 293.9, 45.8 N

[56] References Cited

U.S. PATENT DOCUMENTS

| B 408,123 | 4/1976 | Randell et al. | 260/293.88 |
|---|---|---|---|
| 591,483 | 10/1897 | Merling | 260/293.88 |
| 3,640,928 | 2/1972 | Murayama et al. | 260/23 XA |
| 3,705,166 | 12/1972 | Murayama et al. | 260/45.8 N |
| 3,759,926 | 9/1973 | Chalmers et al. | 260/293.9 |
| 3,840,494 | 10/1974 | Murayama et al. | 260/45.8 N |
| 3,904,581 | 9/1975 | Murayama et al. | 260/45.8 N |
| 3,907,803 | 9/1975 | Ramey et al. | 260/45.8 N |

FOREIGN PATENT DOCUMENTS 44-13945   5/1969   Japan.

OTHER PUBLICATIONS

Textbook of Organic Chemistry—Noller–p. 245, 1961.

*Primary Examiner*—V.P. Hoke
*Attorney, Agent, or Firm*—Connolly and Hutz

[57] ABSTRACT

Cyanamides which may be obtained by reacting cyanogen chloride with certain piperidines can be used as stabilizers for synthetic polymers against discoloration and degradation under the effects of visible and/or UV-light, heat and/or atmospheric influences.

7 Claims, No Drawings

CYANAMIDE STABILIZERS

This invention relates to new cyanamides, to their production and to their use as stabilisers for synthetic polymers.

By virtue of their outstanding properties, the synthetic polymers are widely used, for example as filaments, fibres, films, lacquers or sheeting. Unfortunately, one disadvantage of these synthetic polymers is their poor stability to light and heat. Polyolefin, polyamide and polyurethane elastomers, for example, undergo considerable degradation under the effect of light and heat which is reflected in the loss of their favourable mechanical properties and also in occasionally very considerable discoloration.

Accordingly, a number of different stabilisers such as, for example, phenol derivatives, benzophenone compounds or derivatives of benztriazole have been proposed for stabilising these synthetic polymers. Unfortunately, these products are not entirely satisfactory.

It has now been found that compounds corresponding to the general formula (I) provide synthetic polymers with an excellent degree of protection against degradation.

The new cyanamides are compounds corresponding to the general formula:

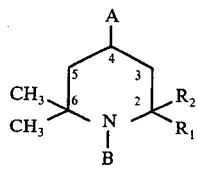

(I)

in which (1) A represents an O—$R_3$ group where $R_3$ represents a straight-chain or branched aliphatic acyl radical having 2 to 20 carbon atoms, an aromatic acyl radical having 7 to 12 carbon atoms or hydrogen, an

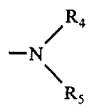

group, where $R_4$ and $R_5$ may be the same or different and each represents a straight-chain or branched alkyl radical having 1 to 20 carbon atoms, a straight-chain or branched aliphatic acyl radical having 2 to 20 carbon atoms or an aromatic acyl radical having 7 to 12 carbon atoms, in addition to which $R_5$ may also represent H, or A may represent, together with the carbon atom in the 4 position of the piperidine ring, a >C=O group where B is a cyano group, or (2) represents a group

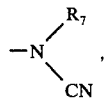

where $R_7$ represents H, a straight-chain or branched alkyl radical having 1 to 20 carbon atoms, a cycloalkyl radical having 5 to 12 carbon atoms, an aralkyl radical having 7 to 12 carbon atoms, a β-cyanoethyl radical, a β-alkoxy carbonyl ethyl radical having 1 to 3 carbon atoms in the alkoxy moiety, an optionally substituted aryl radical having 6 to 14 carbon atoms, or the group —$CH_2$—$CHR_6$—OH, where $R_6$ represents H, methyl or phenyl, where B represents H, a straight-chain or branched alkyl radical having 1 to 20 carbon atoms, an alkenyl or alkinyl radical having 3 to 12 carbon atoms, an aralkyl radical having 7 to 12 carbon atoms or the group —$CH_2$—$CHR_6$—OH, where $R_6$ represents H, methyl or phenyl, and $R_1$ and $R_2$ are the same or different and each represents a straight-chain or branched alkyl radical having 1 to 12 carbon atoms or, together with the ring carbon atom to which they are attached, form a cycloalkyl ring having 5 to 12 carbon atoms.

Examples of the radicals $R_1$ and $R_2$ include methyl, ethyl, n-propyl, isopropyl, n-butyl, sec.-butyl, n-hexyl, n-octyl and n-dodecyl, but preferably alkyl radicals having 1 to 4 carbon atoms, methyl radicals being particularly preferred.

Examples of $R_1$ and $R_2$, which form a cycloalkyl ring with the ring carbon atom to which they are attached, are spirocyclopentyl, spirocyclohexyl, methyl spirocyclohexyl, spirocycloheptyl and spirocyclododecyl, preferably spirocyclohexyl.

Examples of the radical B are CN, H, the methyl, ethyl, n-propyl, isopropyl, n-butyl, sec.-butyl, n-hexyl, n-octyl, n-dodecyl, allyl, α-methallyl, prop-2-inyl, benzyl, α-methyl benzyl, α-naphthyl methyl, β-hydroxy ethyl, β-hydroxy propyl or β-hydroxy phenyl ethyl groups. B preferably represents hydrogen, cyano or a straight-chain or branched alkyl radical having 1 to 4 carbon atoms, H, cyano and the methyl group being particularly preferred. However, B is only cyano when A is a radical as defined in (1) above.

Examples of the radical $R_3$ include H, the acetyl, propionyl, n-butyryl, isobutyryl, n-valerianyl, isovalerianyl, methyl ethyl acetyl, stearoyl, benzoyl, 2-methyl benzoyl, 3-methyl benzoyl, 4-methyl benzoyl and the naphthoyl group. $R_3$ preferably represents H, acetyl, propionyl, n-butyryl, stearoyl and benzoyl, H, acetyl, propionyl and benzoyl being particularly preferred.

Examples of the radicals $R_4$ and $R_5$ include H (in the case of $R_5$ only), methyl, ethyl, propyl, isopropyl, n-butyl, sec.-butyl, tert.-butyl, n-hexyl, octyl and stearyl; H, methyl, ethyl and propyl being preferred. Further examples of $R_4$ are aliphatic or aromatic acid radicals, such as acetyl, propionyl, n-butyryl, isobutyryl, n-valerianyl, isovalerianyl, methyl ethyl acetyl, stearoyl, benzoyl, methyl benzoyl or naphthoyl radicals, acetyl, propionyl, n-butyryl, stearoyl and benzoyl being preferred. Acetyl, propionyl and benzoyl are particularly preferred.

Examples of the radical $R_7$ include H, straight-chain or branched alkyl groups such as methyl, ethyl, n-propyl, isopropyl, n-butyl, sec.-butyl, tert-butyl, octyl or stearyl; cycloalkyl radicals such as cyclopentyl, cyclohexyl, methyl cyclohexyl or cyclododecyl; aralkyl groups such as benzyl or phenyl ethyl; also the β-cyanoethyl group and alkoxy carbonyl ethyl radicals such as 2-methoxy carbonyl ethyl or 2-isopropoxy carbonyl ethyl; aryl radicals such as phenyl, naphthyl and alkyl-, alkoxy-, halogen- or hydroxy-substituted aryl groups such as tolyl, tert-butyl phenyl, octyl phenyl, methoxy phenyl, butoxy phenyl, chlorophenyl, hydroxy phenyl and, in addition, hydroxy alkyl radicals such as β-hydroxy ethyl, β-hydroxy propyl and β-hydroxy-β-phenyl ethyl. $R_7$ preferably represents hydrogen, straight-chain or branched alkyl groups having 1 to 8 carbon atoms such as methyl, ethyl, n-propyl, isopropyl, n-butyl, sec-butyl and octyl; also cyclohexyl and methyl cyclohexyl, benzyl, β-cyanoethyl, 2-methoxy carbonyl ethyl phenyl, tolyl, chlorophenyl and β-hydroxy ethyl. Hydrogen, methyl, cyclohexyl, benzyl and β-hydroxy ethyl are particularly preferred.

The following compounds are mentioned by way of example:

1-cyano-4-oxo-2,2,6,6-tetramethyl piperidine
4-cyanamido-2,2,6,6-tetramethyl piperidine
4-cyanamido-1,2,2,6,6-pentamethyl piperidine
4-cyanamido-1-allyl-2,2,6,6-tetramethyl piperidine
4-cyanamido-1-β-hydroxyethyl-2,2,6,6-tetramethyl piperidine
4-(N-methyl-N-cyano)-amino-2,2,6,6-tetramethyl piperidine
4-(N-benzyl-N-cyano)-amino-2,2,6,6-tetramethyl piperidine
4-cyanamido-1-aza-2,2-dimethyl-spiro[5,5]-undecane
4-(N-phenyl-N-cyano)-amino-2,2,6,6-tetramethyl piperidine
4-(N-methoxycarbonylethyl-N-cyano)-amino-2,2,6,6-tetramethyl piperidine
4-(N-isopropyl-N-cyano)-amino-1,2,2,6,6-pentamethyl piperidine
4-(N-stearyl-N-cyano)-amino-2,2,6,6-tetramethyl piperidine
4-(N-cyclohexyl-N-cyano)-amino-2,2,6,6-tetramethyl piperidine
4-(N-naphthyl-N-cyano)-amino-2,2,6,6-tetramethyl piperidine
4-(N-β-cyanoethyl-N-cyano)-amino-2,2,6,6-tetramethyl piperidine
4-(n-β-hydroxyethyl-N-cyano)-amino-2,2,6,6-tetramethyl piperidine
4-(N-β-hydroxyethyl-N-cyano)-amino-1,2,2,6,6-pentamethyl piperidine
4-(N-β-hydroxypropyl-N-cyano)-amino-1-aza-2,2-dimethylspiro[5,5]-undecane
4-(N,N-dimethyl)-1-cyano-2,2,6,6-tetramethyl piperidine
4-(N-methyl-N-ethyl)-1-cyano-2,2,6,6-tetramethyl piperidine
4-(N,N,-diisopropyl)-1-cyano-2,2,6,6-tetramethyl piperidine
4-(N-stearyl-N-methyl)-1-cyano-2,2,6,6-tetramethyl piperidine
4-(N-acetyl)-1-cyano-2,2,6,6-tetramethyl piperidine
4-(N-propionyl)-1-cyano-2,2,6,6-tetramethyl piperidine
4-(N-methylethyl-acetyl)-1-cyano-2,2,6,6-tetramethyl piperidine
4-(N-benzoyl)-1-cyano-2,2,6,6-tetramethyl piperidine
4-(N-naphthoyl)-1-cyano-2,2,6,6-tetramethyl piperidine
4-(N-benzoyl-N-methyl)-1-cyano-2,2,6,6-tetramethyl piperidine
1-cyano-4-hydroxy-2,2,6,6-tetramethyl piperidine
1-cyano-4-acetoxy-2,2,6,6-tetramethyl piperidine
1-cyano-4-propoxy-2,2,6,6-tetramethyl piperidine
1-cyano-4-methylethyl-acetoxy-2,2,6,6-tetramethyl piperidine
1-cyano-4-stearoyloxy-2,2,6,6-tetramethyl piperidine
1-cyano-4-benzoyloxy-2,2,6,6-tetramethyl piperidine
1-cyano-4-β-naphthoyloxy-2,2,6,6-tetramethyl piperidine The present invention also relates to the production of compounds corresponding to general formula (I) above by reacting cyanogen chloride with piperidines corresponding to the general formula (II) or (III):

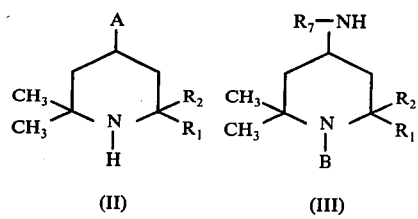

(II)   (III)

The radicals $R_1$, $R_2$ and $R_7$ are as defined above. The radical A represents those groups defined above at (1) in which B represents a cyano group. B represents the radicals mentioned above except for the cyano group.

The reaction may be illustrated by the following general equations:

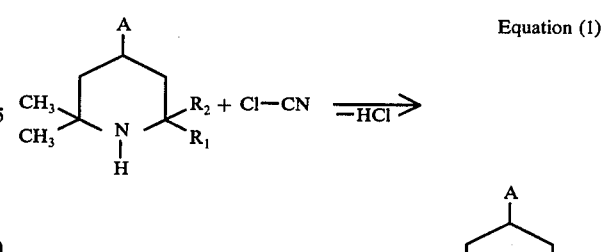

Equation (1)

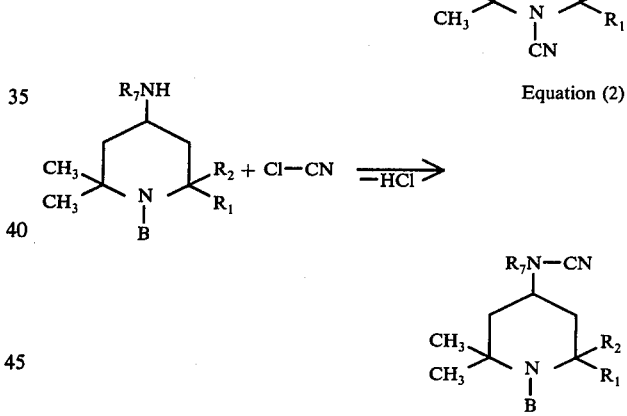

Equation (2)

If, in equation (2), B represents hydrogen, it is preferably the —$NR_7H$-group which reacts.

The reaction of the cyanogen chloride with the known piperidine derivatives of general formulae (II) and (III) in accordance with the invention is carried out by initially introducing into a reaction vessel the piperidine derivative in an inert organic solvent, adding one equivalent of a base for binding the hydrogen chloride formed during the reaction and then adding the cyanogen chloride dropwise at temperatures in the range of from −20° to +10° C and, with particular preference, at temperatures in the range of from −5° to +5° C. From 0.5 to 2.0 moles, preferably from 0.9 to 1.2 moles and, with particular preference, 1 mole of piperidine derivative is used per mole of cyanogen chloride.

Examples of suitable bases are tertiary amines such as, for example, trimethyl amine, triethyl amine or N,N-dimethyl benzyl amine, and also carbonates, oxides and hydroxides of the alkali and alkaline earth metals.

It is preferred to use hydroxides of the alkali and alkaline earth metals, sodium and potassium hydroxide being particularly preferred.

Suitable inert organic solvents in which the reaction according to the invention may be carried out are, for example, petroleum ether, pentane, hexane, cyclohexane, benzene, toluene, xylene, chlorobenzene, o-dichlorobenzene, methylene chloride, diethyl ether, diisopropyl ether, dioxane, tetrahydrofuran and dimethoxy ethane.

In one preferred embodiment, the reaction is carried out in a two-phase system consisting of an aqueous phase and an organic phase. The organic phase consists of the piperidine derivative of general formula (II) or (III) used as starting material and, optionally, an inert water-immiscible organic solvent such as, for example, petroleum ether, pentane, hexane, cyclohexane, benzene, toluene, xylene, chlorobenzene, o-dichlorobenzene, methylene chloride, chloroform, carbon tetrachloride, diisopropyl ether, 1,2-dichloroethane, 1,2-dichloropropane, trichloroethylene, etc.

Substantially insoluble reaction products are separated off by filtration. Following removal of the solvent by evaporation, reaction products which have remained dissolved in the organic phase are purified either by distillation or by recrystallisation.

In general, the reaction is carried out under normal pressure. However, it may also be carried out under reduced pressure or under an elevated pressure of up to about 10 bars, preferably up to about 2 bars.

The process may, of course, also be carried out continuously, for example in a tubular reactor, in a cascade of reaction vessels or in any other apparatus of the type commonly used for carrying out continuous processes.

The invention also relates to the use of the compounds corresponding to formula (I) as stabilisers for synthetic polymers and to the polymers thus stabilised.

The expression "synthetic polymers" covers the following products but is not restricted to these: polyurethanes, polyethylene oxide, polypropylene oxide and polyepoxide polymers, polyamides, for example nylon 4, nylon 6, nylon 11, nylon 12, nylon 6,6, nylon 6,10 or copolyamides of the above components; aromatic polyamides, for example, isophthalic acid and terephthalic acid, m-phenylene diamine and/or p-phenylene diamine; polyesters such as polyethylene terephthalate, polybutylene terephthalate or segmented copolyether esters of dihydroxy polytetramethylene oxide, terephthalic acid/isophthalic acid ethylene glycol/1,4-butane diol and 1,4-cyclohexane diol; polycarbonates; polyimides; plastics based on cellulose such as, for example, cellulose acetate, cellulose butyrate or polyacetals such as polyoxymethylene; polyolefins such as polyethylene of low or high density, polypropylene, polystyrene, polybutadiene, polyisoprene, polypentenamers, polyacrylonitrile, also homopolymers of other olefins and copolymers such as ethylene/propylene copolymers, ethylene/propylene diene copolymers, ethylene/butylene copolymers, ethylene/vinyl acetate copolymers, styrene/butadiene copolymers, styrene/acrylonitrile copolymers, acrylonitrile/butadiene/styrene copolymers; polyvinyl chloride and polyvinylidene chloride; copolymers of vinyl chloride with vinylidene chloride and copolymers of vinyl chloride and vinylidene chloride with vinyl acetate and other olefins such as acrylonitrile, for example; and unsaturated polyester resins.

One particularly important group of polymers to be stabilised are the elastic polyurethanes which may optionally be present in foamed form and which may be produced by methods known per se from conventional starting materials. The polyurethanes are generally obtained by reacting relatively high molecular weight polyhydroxyl compounds (for example polyesters or polyethers with a molecular weight of about 500 to 5000 and with melting points preferably below 60° C) and aliphatic araliphatic or aromatic polyisocyanates (preferably aromatic diisocyanates, such as tolylene diisocyanate or diphenyl methane-4,4'-diisocyanate), also so-called chain-extending agents, i.e. low molecular weight compounds (molecular weight for example 18 to 400) containing 2 or more isocyanate-reactive groups (for example water, low molecular weight diols, diamines, dihydrazides or similar compounds such as, for example, amino alcohols, amino hydrazides, hydroxy hydrazides, amino semicarbazides, semicarbazide hydrazides, semicarbazide carbazinic esters or corresponding mixtures of these chain-extending agents produced in one or several stages either in the melt or in solvents by a number of known and modifiable processes.

The following are mentioned as examples of starting materials for producing the above-mentioned polyurethanes: polyesters of adipic acid and dialcohols having from 2 to about 10 carbon atoms, preferably those with more than 5 carbon atoms, the dialcohols also being usable for lowering the melting points of the polyesters in the mixture; polyesters of caprolactone and dialcohols, also polyalkylene ether diols, especially polytetramethylene ether diols, polytrimethylene ether diols, polypropylene glycol or corresponding copolyethers. Preferred diisocyanates are aromatic diisocyanates such as diphenyl methane-4,4'-diisocyanate, tolylene diisocyanate, araliphatic diisocyanates such as m-xylylene diisocyanate or even aliphatic diisocyanates, such as hexamethylene diisocyanate and dicyclohexyl methane-4,4'-diisocyanate. These starting materials are reacted, optionally with additional dialcohols, to form NCO-preadducts which preferably have the structures indicated in Belgian Patent Specification No. 734.194. Suitable chain-extending agents, which may optionally be used in admixture or in a multistage reaction, are water and/or dialcohols or trialcohols, such as butane diol and p-xylylene glycols, trimethylol propane, amino alcohols such as ethanolamine, diamines such as diphenyl methane-4,4'-diamine or 3,3'-dichlorodiphenyl methane-4,4'-diamine, but preferably aliphatic diamines such as ethylene diamine, 1,2-propylene diamine, isophorone diamine, metaxylylene diamine and hydrazine or dihydrazides, such as carbodihydrazide, oxalic acid dihydrazide, glutaric acid dihydrazide, pimelic acid dihydrazide, terephthalic acid dihydrazide, β-alanyl hydrazide or semicarbazide hydrazides, such as β-semicarbazide alanyl hydrazide.

It is preferred to stabilise polyurethanes which, in addition to urethane groups, also contain —NH—CO—NH— groups formed by the reaction of isocyanate groups with water and/or with compounds containing terminal $NH_2$-groups (for example diamines, dihydrazides, carbodihydrazide, semicarbazide hydrazides or hydrazine) and which have a substantially linear, segmented molecular structure, are soluble in highly polar solvents, such as dimethyl formamide or dimethyl acetamide, before they are formed or shaped, and of which the characteristic segments may be characterised by the following formula moiety:

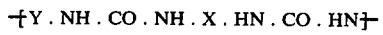

This segment may be formed from the reaction of an NCO-preadduct OCN.Y.NCO with a chain-extending agent H₂N.X.NH₂.

The radical —Y— of the NCO-preadduct may be built up, for example, as follows:

or may have any other normal composition (cf. Belgian Patent Specification No. 734,194).

In the above formula, R represents a difunctional aliphatic, araliphatic or aromatic radical (of a diisocyanate), D represents the radical of a relatively high molecular weight polyhydroxyl compound, having a molecular weight in the range of from 500 to 5000 and with melting points below 60° C, without its terminal hydroxyl groups (for example the radical of a polyalkylene ether, polyester, polyacetal or poly-N-alkylurethane). X is the radical of a difunctional chain extender containing terminal NH₂-groups without the terminal NH₂-groups, for example an aliphatic, araliphatic, aromatic or heterocyclic radical, an —HN—CO-alkylene-CO—NH-radical, an —NH—CO—NH—(CH₂)₂—CO—NH— radical or a bond between two N-atoms. The synthesis of polyurethane (ureas) of this type is described in detail, for example in German Auslegeschrift No. 1,270,276 and in Belgian Patent Specification No. 734,194. Polyurethane foams can be produced, for example with the stabilisers added to the starting components (for example polyethers), by known methods and according to known recipes (cf. for example Kunststoff-Handbuch, Vol. VII, Polyurethane, Carl Hanser Verlag Munich, 1966, pages 440 to 457, 504 to 531).

The stabilisers are used in particular for stabilising synthetic polymers against discoloration and degradation under the effects of visible and/or UV-light, heat and/or atmospheric influences such as oxygen, oxides of nitrogen, chlorine and exhaust combustion gases.

The compounds of general formula (I) used as stabilisers in accordance with the invention may readily be incorporated into synthetic polymers by any of the standard processes for compounding additives in a polymer. For example, the liquid, molten or solid powder-form stabiliser may be mixed with the synthetic polymer or may be mixed in the form of a solution, suspension or emulsion with a melt, solution, suspension or emulsion of the synthetic polymer. Mixing may optionally be carried out during the actual preparation of the polymer. In the case of filaments, the stabiliser may even be applied to the surface in the form of a melt of the preparation or may be incorporated during wet spinning from the coagulation bath with the filaments in gel form.

The quantity in which the stabiliser is used in accordance with the invention is governed by the type and particular application of the polymer and may be left to the discretion of the average expert. In general, the stabiliser is used in a quantity of from 0.01 to 5% by weight, preferably in a quantity of from 0.05 to 3.5% by weight and, with particular preference, in a quantity of from 0.05 to 2.5% by weight, based on the quantity of polymer.

In addition to the stabilisers according to the invention, other known additives may be incorporated in the polymer. Additives such as these include antioxidants of the sterically hindered phenol type such as, for example, 2,6-di-tert-butyl-p-cresol; 4,4'-thiobis-(6-tert-butyl-3-methyl phenol; 2,2'-thiobis-(6-tert-butyl-4-methyl phenol); α,α'-bis-(2-hydroxy-3,5-dialkyl phenyl)-p-diisopropyl benzenes; α,α'-bis-(2-hydroxy-3,5-dialkyl phenyl)-m-diisopropyl benzenes; 2,2'-methylene-bis-(4-methyl-6-tert-butyl phenol); 2,2'-methylene-bis-(4-methyl-6-cyclohexyl phenol); 1,1,3-tris-(5-tert-butyl-4-hydroxy-2-methyl phenyl)-butane; tetrakis-(3,5-di-tert-butyl-4-hydroxy phenyl propionyl oxymethyl)-methane; also compounds of divalent sulphur such as, for example, dilauryl thiodipropionate; compounds of trivalent phosphorus such as, for example, triphenyl phosphite, tris-(p-nonyl phenyl)-phosphite, also UV-absorbers based on 2-(2'-hydroxy phenyl)-benzotriazole such as, for example, 2-(2'-hydroxy-5'-methyl phenyl)-benzotriazole, 2-(3',5'-di-tert-butyl-2'-hydroxy phenyl)-5-chlorobenzotriazole; or even UV-absorbers based on benzophenone such as, for example, 2-hydroxy-4-octoxy benzophenone; 2',4'-di-tert-butylphenyl-3,5-di-tert-butyl-4-hydroxy benzoate; cyanoacylic acid esters such as, for example, α-cyano-β-methyl-β-(p-methoxy phenyl)-acrylate and other light stabilisers such as, for example, 2,2'-thiobis-(4-tert-octyl phenolate)-n-butyl amine nickel.

It is even possible to use two or more of the cyanamides according to the invention at the same time as stabilisers.

The compounds according to the invention may also be used as intermediate products for the production of pharmaceutically active compounds or plant protection agents. They are also effective as polymerisation inhibitors.

The object of the following Examples is merely to illustrate the invention. The structures of the compounds are clearly identified by their nuclear resonance and mass spectra. M⁺ is the abbreviation for the mass of the mole ion in the mass spectra. All parts and percentages are by weight unless otherwise indicated.

EXAMPLE 1

4-Cyanamido-2,2,6,6-tetramethyl piperidine 156 g (1 mole) of 4-amino-2,2,6,6-tetramethyl piperidine are dissolved in 500 ml of methylene chloride, 40 g (1 mole) of sodium hydroxide in 500 ml of water are introduced and 51 ml of cyanogen chloride are added dropwise at a temperature of 0° to 5° C. The mixture is stirred until it reaches room temperature, after which 4-cyanamido-2,2,6,6-tetramethyl piperidine, which melts at 240° C, is filtered off in a yield of 166 g (corresponding to 91.5% of the theoretical).

$C_{10}$—$H_{19}N_3$ (181.3) observed M⁺ 181

EXAMPLE 2

4-(N-Methyl-N-cyano)-amino-2,2,6,6-tetramethyl piperidine 170 g (1 mole) of 4-N-methyl amino-2,2,6,6-tetramethyl piperidine are dissolved in 500 ml of methylene chloride, 40 g (1 mole) of sodium hydroxide in 500 ml of water are introduced and 51 ml of cyanogen chloride are added dropwise at 0° to 5° C. The mixture is stirred until it reaches room temperature, after which the organic phase is separated off, dried over sodium sulphate, filtered off and the methylene chloride distilled off, leaving as a residue 162 g (83% of the theoretical) of 4-(N-methyl-N-cyano)-amino-2,2,6,6-tetramethyl piperidine melting at 73° to 77° C.

$C_{11}H_{21}N_3$ (195.3) observed $M^+$ 195

EXAMPLE 3

4-(N-Cyclohexyl-N-cyano)-amino-2,2,6,6-tetramethyl piperidine melting at 123° C is obtained in the same way as in Example 2 using 4-cyclohexyl amino-2,2,6,6-tetramethyl piperidine.

$C_{16}H_{29}N_3$ (263.4) observed $M^+$ 263

EXAMPLE 4

4-(N-Benzyl-N-cyano)-amino-2,2,6,6-tetramethyl piperidine melting at 215° to 219° C is obtained in the same way as in Example 2 using 4-benzyl amino-2,2,6,6-tetramethyl piperidine $C_{17}H_{25}N_3$ (271.4) observed $M^+$ 271

EXAMPLE 5

1-Cyano-4-oxo-2,2,6,6-tetramethyl piperidine 86.5 g (0.5 mole) of triacetone amine monohydrate are dissolved in 250 ml of methylene chloride, a solution of 20 g (0.5 mole) of sodium hydroxide in 250 ml of water is introduced and 26 ml of cyanogen chloride are added dropwise at 0° to 5° C. The mixture is stirred until it reaches room temperature, after which the organic phase is separated off, dried over sodium sulphate, filtered off and the methylene chloride distilled off. Distillation in a high vacuum gives the pure 1-cyano-4-oxo-2,2,6,6-tetramethyl piperidine. It boils (bp $_{0.15}$) at 100° to 105° C and melts at 75° to 76° C.

Yield: 71 g (79% of the theoretical)

$C_{10}H_{16}N_2O$ (180.3) observed $M^+$ 180

Example 6

1-Cyano-4-hydroxy-2,2,6,6-tetramethyl piperidine 62.8 g (0.4 mole) of 4-hydroxy-2,2,6,6-tetramethyl piperidine are dissolved in 250 ml of methylene chloride a solution of 16 g (0.4 mole) of sodium hydroxide in 250 ml of water is introduced and 20.5 ml of cyanogen chloride are added dropwise to the mixture at 0° to 5° C. The mixture is stirred until it reaches room temperature, after which the organic phase is separated off, dried with sodium sulphate, filtered and the methylene chloride distilled off, leaving 31 g (42.5% of the theoretical) of 1-cyano-4-hydroxy-2,2,6,6-tetramethyl piperidine. Bp $_{0.5}$ = 135° C; melting point 96°–98° C.

$C_{10}H_{18}N_2O$ (182.3) observed $M^+$ 182

EXAMPLE 7

1-Cyano-4-benzoyloxy-2,2,6,6-tetramethyl piperidine 104.5 g (0.4 mole) of 4-benzoyloxy-2,2,6,6-tetramethyl piperidine are dissolved in 400 ml of methylene chloride, 400 ml of 1N sodium hydroxide are introduced and 21 ml of cyanogen chloride are added dropwise over a period of 30 minutes with cooling at −5° to −5° C. The cooling is then removed and the mixture is stirred until it reaches room temperature. The organic phase is separated off, dried with sodium sulphate, filtered and the methylene chloride distilled off. Recrystallisation from acetonitrile gives 94 g (82% of the theoretical) of 1-cyano-4-benzoyloxy-2,2,6,6-tetramethyl piperidine melting at 150° to 152° C. The IR-spectrum no longer shows an NH-band, but instead a nitrile band at 2170 cm$^{-1}$ and a carbonyl band at 1700 cm$^{-1}$.

$C_{17}H_{22}N_2O_2$ (286.4) observed $M^-$ 286

EXAMPLE 8

1-Cyano-4-,N,N-dimethylamino-2,2,6,6-tetramethyl piperidine 85 g (0.5 mole) of 4-N,N-dimethyl amino-2,2,6,6-tetramethyl piperidine are dissolved in 500 ml of methylene chloride, 500 ml of 1N sodium hydroxide are introduced and 25.5 ml of cyanogen chloride are added dropwise with stirring over a period of 25 minutes at −5° to +5° C. The cooling is then removed and the mixture is stirred until it reaches room temperature. After stirring for another 3 hours at room temperature, the organic phase is separated off, dried over sodium sulphate, filtered off and the methylene chloride and excess starting material (bp$_{10}$ 90°–98° C) distilled off in vacuo. The 1-cyano-4-N,N-dimethylamino-2,2,6,6-tetramethyl piperidine is then distilled in a high vacuum. It has a boiling point of 100° to 115° C at 0.1 Torr and a melting point of 102°–104° C. It no longer shows an NH-band in the infrared spectrum, but instead a cyano band at 2160 cm$^{-1}$.

$C_{12}H_{23}N_3$ (209.3) observed $M^-$ 209

EXAMPLE 9

1-Cyano-4-benzoylamino-2,2,6,6-tetramethyl piperidine 130 g (0.5 mole) of 4-benzoylamino-2,2,6,6-tetramethyl piperidine are dissolved in 500 ml of methylene chloride, the resulting solution is cooled to −10° C and 500 ml of 1N sodium hydroxide are added. 25.5 ml of cyanogen chloride are then added dropwise at 0° to 5° C. After the cooling has been removed, the mixture is stirred for 6 hours at room temperature. The organic phase is separated off, dried with sodium sulphate, the methylene chloride is distilled off and 100 ml of petroleum ether are added to the residual honey-like substance. The crystals then formed are filtered off after a while.

Melting point 228°–229.5° C

IR-spectrum (KBr): NH at 3270 cm$^{-1}$

CN at 2185 cm$^{-1}$; CO at 1630 cm$^{-1}$ $C_{17}H_{23}N_3O$ (285.4) observed $M^-$ 285

EXAMPLE 10

(a) Procedure for producing the polyurethane to be stabilised 1000 parts of adipic acid/1,6-hexane diol/2,2;1 -dimethyl propane diol mixed polyester (molar ratio of the glycols 65 : 35) with a molecular weight of 1860 are mixed with 19.8 parts of N-methyl-bis-(β-hydroxypropyl)-amine, 280.7 parts of diphenyl methane-4,4'-diisocyanate and 328 parts of dimethyl formamide, and the resulting mixture is heated for 72 minutes to 45°–50° C. After cooling to room temperature, the NCO-prepolymer formed has an NCO content of 2.92% (based on solids). 748 parts of this prepolymer solution are introduced with stirring into a solution of 33.7 parts of $H_2N.NH.CO.NH.CH_2.CO.NH.NH_2$ in 67 parts of water and 1570 parts of dimethyl formamide. The homogeneous viscous solution is pigmented with 4% of rutile, based on solids, and has a viscosity of 440 poises at 25° C.

(b) Measurement of the Stabilising Effect Using Elastomer Films and (cut) Filaments The stabilisers and comparison substances are added (in the form of a concentrated solution in dimethyl formamide) to the elastomer solutions in the quantities specified, followed by stirring for the purposes of homogenisation, after which the solutions are processed into the shaped articles.

The solutions are preferably coated onto glass plates in layer thicknesses of about 0.2 mm and dried in a drying cabinet at 70° to 100° C to form films.

In a screening test the films can be cut into approximately 1 cm wide strips and exposed to light in a Fadeometer (assessment of discoloration and the qualitative manifestation of degradation on exposure to light).

The films are preferably cut in a film-cutting machine into rectangular filaments with an overall denier of about 200 to 300 dtex and exposed to light in the form of these cut filaments. On account of the large surface of the filaments, the damage caused by the action of light is more intensive and substantially equivalent to the behaviour of filaments spun on an industrial scale. The solutions can also be wet spun or dry spun.

(c) Stabiliser Additions and Stabilising Effect

The quantities of stabiliser specified are added to the polyurethane (urea) elastomer solutions a), the solutions are dried to form films and the films, after cutting into filaments, are exposed to light in a Fadeometer and (in some cases) tested for tensile strength, elongation at break and discoloration (cf. Table 1).

The elastomer solutions containing 2% of stabiliser (3) were processed into elastomer filaments both by the dry spinning process and by the wet spinning process. These filaments showed substantially the same resistance to discoloration and approximately the same half lives of their tensile strength values after exposure to UV-light as the filaments cut from films.

The stabilising additives have a distinct stabilising effect against deterioration of tensile strength, against reduction in elongation at break and, in particular, against discoloration under the effect of light.

nisable in the case of the stabiliser according to Example (3). This effect of the stabilisers in outstanding, but what is particularly surprising is the minimal dependence upon concentration and the considerable effectiveness even at relatively low concentrations.

This behaviour is scarcely shown by the usual phenolic stabiliser which are preferably used in synergistic combinations with UV-absorbers.

Surprisingly, the tetramethyl piperidine compounds do not bring about the distinct molecular degradation typical of secondary amines, but instead have a certain heat-stabilising effect in the polyurethanes at high temperatures (for example 1 hour/130° C or 30 seconds at 180° C).

However, the effectiveness of the stabiliser is dependent to a fairly marked extent upon its overall structure. As shown in Table 3, structurally similar, known compounds from the tetramethyl piperidine series (cf. Table 2, A-D) have a much weaker stabilising effect than the cyanamide derivatives according to the invention (Examples 1 to 4).

Table 2

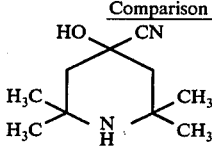

Comparison Substances:

A — according to FR 1,360,030, FR 1,526,656, US 3,334,103

B — according to DT-OS 2,349,962

C — according to DT-OS 2,349,962

Table 1

Tensile strength/elongation at break and discoloration of cut filaments of PU-elastomers with and without additions of stabiliser

| Stabiliser according to Example No. x) | Quantity of stabiliser added(based on solids)(%) | Tensile strength/elongation at break (cN/dtex) (%) and discoloration after Fadeometer testing for | | | | |
|---|---|---|---|---|---|---|
| | | 0 | 22 | 44 | 66 | 88 hours |
| no stabiliser added | 0 | 0.53/620 colourless | 0.37/525 yellowish-yellow | 0.22/436 yellow | n.m. yellow brown | n.m. yellow brown |
| 1 | 2.0 | 046/580 colourless | 0.43/560 colourless | 0.36/485 almost colourless | 0.30/465 almost colourless | 0.23/425 almost colourless to pale yellowish |
| 2 | 2.0 | 0.66/605 colourless | 0.42/586 colourless | 0.30/490 almost colourless | 0.18/356 almost colourless; pale yellowish | 0.11/232 yellow |
| 3 | 2.0 | 0.54/660 colourless | 0.51/645 colourless | 0.42/585 colourless | 0.34/510 almost colourless | 0.29/470 almost colourless |
| 3 | 1.0 | colourless | colourless | colourless | almost colourless | almost colourless |
| 3 | 0.5 | colourless | colourless | colourless | almost colourless | almost colourless-pale yellowish |
| 3 | 0.25 | colourless | colourless | colourless | pale yellowish | pale yellowish |
| 3 plus 1% Irganox 1010 | | colourless | colourless | colourless | colourless | colourless |
| 4 | 2.0 | colourless | colourless | almost colourless | almost colourless | pale yellowish after 154 hours |

(n.m. = cannot be measured(tensile strength below 0.1 cN/dtex; elongation at break below 200%)

In the case of tensile strength, the half life of degradation is increased by exposure from about 25 hours to 66–68 hours, whilst the tendency towards discoloration is considerably reduced. Even after 154 hours in the Fadeometer, distinct colour stabilisation was still recog-

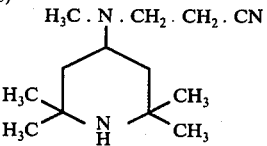

Table 2-continued

| Comparison Substances: | |
|---|---|
| D   H.N.H. with 2,2,6,6-tetramethyl-4-aminopiperidine structure | according to US 3,147,268 NL 7,313,683 |

Table 3

Tensile strength/elongation at break and discoloration of cut filaments of PU-elastomers using partly known compounds of the tetramethyl piperidine series Comparison Tests
Tensile strength/elongation at break and discoloration (cN/dtex) (%) after Fadeometer testing for

| Comparison substance (cf.Table 2) | Quantity (%) | 0 | 22 | 44 | 66 | 88 hours |
|---|---|---|---|---|---|---|
| A | 2.0 | 0.56/665 colourless | 0.28/490 yellowish | 0.18/422 yellow | yellow-brown | brown-yellow |
| B | 2.0 | colourless | yellow | yellow-brown | yellow-brown | brown-yellow |
| C | 2.0 | colourless | almost colourless | yellow | yellow-brown | brown-yellow |
| D | 2.0 | colourless | yellowish | yellow | yellow-brown | brown-yellow |

As the results show, there is very little, if any, improvement in resistance to degradation or reduction of discoloration in polyurethanes. The stabilisers according to the invention have a considerably better stabilising effect.

EXAMPLE 11

(a) Procedure for Producing the Polyurethane to be Stabilised 718 parts of the NCO-prepolymer described in Example 10 are stirred into a carbon dioxide suspension formed by adding 25 parts of solid carbonic acid to a solution of 1268 parts of ethylene diamine (99 %) in 1578 parts of dimethyl formamide. A highly viscous solution (viscosity approximately 210 poises) is obtained after pigmenting with 4 % of rutile.

(b) Stabilising the Polyurethane

2% of each of the stabilisers according to Examples 1 to 3 are incorporated in the solutions of the PU-elastomer 11 a). Films are cast from the resulting solutions, cut into filaments (denier approximately 300 den.) and tested in a Fadeometer for 0, 22, 44 and 66 hours.

Testing the tensile strength of the filaments by comparison with non-stabilised polyurethane(urea) elastomers produced the following percentage improvement in the half life of the tensile strength values after exposure to UV light (Fadeometer).

| | percentage improvement in half life of tensile strength on exposure to UV-light |
|---|---|
| without stabiliser | 0 |
| 2% of stabiliser according to Example 1 | +40% |
| 2% of stabiliser according to Example 2 | +120% |
| 2% of stabiliser according to Example 3 | +90% |

EXAMPLE 12

The class of compounds containing the 1-N-cyano group (Examples 5 to 9) is incorporated into the elastomer solution 10 a) in the same way as in Example 10 b). Although, in this case too, a stabilising effect is observed when the cut filaments and films are exposed to UV-light, the stabilising effect is distinctly weaker by comparison with the 4-cyanamide derivatives of tetramethyl piperidine.

With additions of 2% by weight of each of the stabilisers according to Examples 5 to 9, the half lives of the degradation of tensile strength are improved by only about 10 to 35%, whereas the 4-cyanamino derivatives gave values improved by about 100 to 250%.

EXAMPLE 13

600 parts of dimethyl terephthalte, 20 parts of dimethyl isophthalate and 980 parts of polytetramethylene glycol (molecular weight 980) are melted with 750 parts of 1,4-butane diol at about 150° to 165° C. The resulting melt is mixed with 0.45 mMole of Ti-(OC$_4$H$_9$)$_4$/(CH$_3$COO)$_2$.Mg and 0.05% by weight of di-$\beta$-naphthyl-p-phenylene diamine and the ester exchange reaction is carried out under atmospheric pressure at 200° to 220° C until the elimination of methanol is over. The temperature is then increased to 250° C, vacuum is applied to an increasing extent and the excess butane diol is distilled off from the mixture under a pressure of about 0.3 to 0.5 Torr. After a polycondensation time of about 75 minutes, the melt is discharged under nitrogen and cooled.

The segmented copolyester ether elastomer is dissolved in hot tetrachloroethane to form a 20 % solution. The stabiliser according to Example 3 is dissolved in portions of the solution in quantities of 2 %, based on solids, and the solutions are dried to form films.

The films (approximately 0.2 mm thick) are exposed to UV-light in a Fadeometer. Whereas the unstabilised film is lemon-yellow in colour after an exposure time of 1320 minutes and has lost its elasticity, i.e. is brittle and breaks very easily, the film containing 2% of stabliser No. 3 is almost colourless and has remained elastic. In the event of longer exposure, the slight yellowing fades; the stablised films only begin to turn brittle after an exposure time of about 2500 minutes.

EXAMPLE 14

A 12% solution of a copolyamide (produced by polycondensing 50 parts by weight of caprolactam, 35 parts by weight of hexamethylene-1,6-diammonium adipate and 20 parts by weight of hexamethylene-1,6-diammonium sebacate) in 85 parts by weight of methanol, 6 parts by weight of isopropanol, 4.5 parts by weight of isobutanol and 4.5 parts by weight of water, is dried to form an approximately 0.10 mm thick film.
(a) without the addition of a stabiliser
(b) with 2% by weight of the stabiliser according to Example 3 added,
and exposed to light for 300 hours in a Fadeometer.

The unstabilised copolyamide (a) turns brittle and breaks when the film is bent, whereas the stabilised film (b) remains flexible.

EXAMPLE 15

400 parts of a polytetramethylene ether diol with a molecular weight of 1045 (POLYMEG 1000, a product of the Quaker Oats Company) are reacted with a solution of 140.8 parts of diphenyl methane-4,4'-diisocyanate and 135 parts of dimethyl formamide at 50° C until the NCO-content amounts to 3.2% (based on the solids content of the prepolymer solution).

6.02 parts of hydrazine hydrate are dissolved in 898 parts of dimethyl formamide, a carbonate suspension of the hydrazine is formed by adding 10 parts of solid carbon dioxide and the suspension thus formed is reacted by stirring in 430 parts of the above NCO-prepolymer solution to form a segmented linear polyurethane. The homogeneous, viscous elastomer solution (51 poises at 20° C) is pigmented with a $TiO_2$-suspension (4% of $TiO_2$/rutile based on elastomer solids).

The solution is cast into elastomer films both with and without (comparison test) additions of stabiliser.

The elastomer films thus produced are Fadeometer-tested in the form of strips (for results, see Table 4). The results show that the unstabilised polyether urethane yellows very quickly and has been degraded after only 22 hours in the Fadeometer (no more strength, surface of the film "crackles" under minimal elongation).

Table 4

| | Fadeometer testing of film strips | | | | |
|---|---|---|---|---|---|
| | after 22 hours | 44 hours | 66 hours | 88 hours | 156 hours |
| without stabiliser | yellow films have no strength and are "crackled". Substantially degraded strength | yellow(brown) Films without strength, totally degraded | yellow-brown | yellow brown films have no strength, totally degraded | totally degraded |
| + 2% by weight of stabiliser No. 3 | colourless strength substantially intact | colourless | colourless | colourless, fully elastic strength substantially intact no "crackling", fully elastic | colourless fully elastic |

EXAMPLE 16

A copolymer of 60 parts by weight of acrylonitrile and 40 parts by weight of vinyl chloride is dissolved in dimethyl formamide at 40° C to form a 22% solution. Portions of the solution with and without additions of stabiliser are cast into approximately 0.15 mm thick films and are subsequently Fadeometer-tested.

Even when the solution is dried into films (about 1 hour/100° C) the unstabilised film turns pale brownish in colour, whereas the film containing 2% by weight of stabiliser No. 3 is colourless. In addition to this heat-stabilising effect, the stabiliser also affords protection against UV-light. After 1320 minutes in the Fadeometer, the stabilized film has not discoloured whereas the discoloration of the unstabilised film has increased.

We claim:

1. Cyanamides corresponding to the general formula (I):

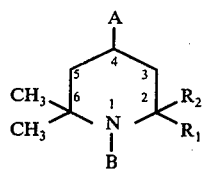

in which (a) where B is a cyano group, A represents an O—$R_3$ group, where $R_3$ represents a straight-chain or branched aliphatic hydrocarbyl carbonyl having 2 to 20 carbon atoms, an aromatic hydrocarbyl having 7 to 12 carbon atoms, or hydrogen, an

group, where $R_4$ and $R_5$ may be the same or different and each represents a straight-chain or branched alkyl having 1 to 20 carbon atoms, a straight-chain or branched aliphatic hydrocarbyl carbonyl having 2 to 20 carbon atoms or an aromatic hydrocarbyl carbonyl having 7 to 12 carbon atoms, in addition to which $R_5$ may also represent H, or A may, together with the carbon atom in the 4 position of the piperidine ring represent a >C=O group, or (b) where B is H, a straight-chain or branched alkyl having 1 to 20 carbon atoms, an alkenyl or alkynyl having 3 to 12 carbon atoms, an aralkyl having 7 to 12 carbon atoms or the group—$CH_2$—$CHR_6$—OH, where $R_6$ represents H, methyl or phenyl, A represents a group

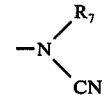

$R_7$ represents H, a straight-chain or branched alkyl having 1 to 20 carbon atoms, a cycloalkyl having 5 to 12 carbon atoms, an aralkyl having 7 to 12 carbon atoms, a β-cyanoethyl, a β-alkoxy carbonyl ethyl having 1 to 3 carbon atoms in the alkoxy moiety, an aryl having 6 to 14 carbon atoms or the group —$CH_2$—$CHR_6$—OH, where $R_6$ represents H, methyl or phenyl, and $R_1$ and $R_2$ may be the same or different and each represents a straight-chain or branched alkyl having 1 to 12 carbon atoms or, together with the ring carbon atom to which they are attached, form a cycloalkyl ring having 5 to 12 carbon atoms.

2. Cyanamides as claimed in claim 1, in which $R_1$ and $R_2$ represent alkyl radicals having 1 to 4 carbon atoms or spirocyclohexyl; $R_3$ represents H, acetyl, propionyl, n-butyryl, stearoyl or benzoyl; $R_4$ and $R_5$ represent acetyl, propionyl, n-butyryl or stearoyl; B represents H, cyano and alkyl having 1 to 4 carbon atoms and when B is H or alkyl of 1–4 carbon atoms, $R_7$ is H, alkyl groups having 1 to 8 carbon atoms, cyclohexyl, methyl cyclohexyl, benzyl, β-cyanoethyl, 2-methoxy carbonyl ethyl, phenyl, tolyl, chlorophenyl or β-hydroxyethyl.

3. Cyanamides as claimed in claim 1, in which $R_1$ and $R_2$ represent methyl radicals; $R_3$ represents H, acetyl, propionyl or benzoyl; $R_4$ and $R_5$ represent acetyl, propionyl orbenzoyl; and B represents H, cyano or methyl and when B is H or methyl $R_7$ is H, methyl, cyclohexyl, benzyl or β-hydroxy ethyl.

4. A process for stabilising synthetic polymers, wherein the polymers have added to them active quantities of cyanamides corresponding to the general formula:

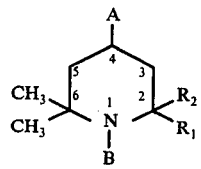

in which
(a) where B is a cyano group, A represents an O — $R_3$ group, where $R_3$ represents a straight-chain or branched aliphatic hydrocarbyl carbonyl having 2 to 20 carbon atoms, an aromatic hydrocarbyl carbonyl having 7 to 12 carbon atoms, or hydrogen, an

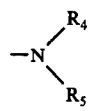

group, where $R_4$ and $R_5$ may be the same or different and each represents a straight-chain or branched alkyl having 1 to 20 carbon atoms, a straight-chain or branched aliphatic hydrocarbyl carbonyl having 2 to 20 carbon atoms or an aromatic hydrocarbyl carbonyl having 7 to 12 carbon atoms, in addition to which $R_5$ may also represent H, or A may, together with the carbon atom in the 4 position of the piperidine ring represent a $>C=O$ group, or (b) where B is H, a straight-chain or branched alkyl radical having 1 to 20 carbon atoms, an alkenyl or alkynyl having 3 to 12 carbon atoms, an aralkyl having 7 to 12 carbon atoms or the group —$CH_2$—$CHR_6$—OH, where $R_6$ represents H, methyl or phenyl, A represents a group

where $R_7$ represents H, a straight-chain or branched alkyl having 1 to 20 carbon atoms, a cycloalkyl having 5 to 12 carbon atoms, an aralkyl having 7 to 12 carbon atoms, a β-cyanoethyl, a β-alkoxy carbonyl ethyl having 1 to 3 carbon atoms in the alkoxy moiety, an aryl having 6 to 14 carbon atoms or the group —$CH_2$—$CHR_6$—OH, where $R_6$ represents H, methyl or phenyl,
and $R_1$ and $R_2$ may be the same or different and each represents a straight-chain or branched alkyl having 1 to 12 carbon atoms or, together with the ring carbon atom to which they are attached, form a cycloalkyl ring having 5 to 12 carbon atoms.

5. A process as claimed in claim 4, wherein the cyanamides are added in quantities of from 0.01 to 5% by weight, based on the polymer.

6. A process as claimed in claim 4, wherein the cyanamides are added in quantities of from 0.05 to 3.5% by weight, based on the polymer.

7. Synthetic polymers stabilised by the process claimed in claim 4.

* * * * *